(12) United States Patent
Lindbäck et al.

(10) Patent No.: US 7,637,859 B2
(45) Date of Patent: Dec. 29, 2009

(54) SLEEPING MODE ACCESSORY

(75) Inventors: Maria Lindbäck, Lund (SE); Rikard Pantorp, Oxie (SE)

(73) Assignee: Sony Ericsson Mobile Communications AB, Lund (SE)

( * ) Notice: Subject to any disclaimer, the term of this patent is extended or adjusted under 35 U.S.C. 154(b) by 237 days.

(21) Appl. No.: 11/760,420

(22) Filed: Jun. 8, 2007

(65) Prior Publication Data

US 2008/0306330 A1 Dec. 11, 2008

(51) Int. Cl.
*A61M 21/00* (2006.01)
(52) U.S. Cl. ....................................................... 600/28
(58) Field of Classification Search ............... 600/26–28
See application file for complete search history.

(56) References Cited

U.S. PATENT DOCUMENTS

| 5,740,812 | A | 4/1998 | Cowan |
| 2005/0070815 | A1 | 3/2005 | Shahrestani et al. |
| 2005/0256416 | A1 | 11/2005 | Chen |
| 2006/0224046 | A1 | 10/2006 | Ramadas et al. |
| 2007/0113725 | A1 | 5/2007 | Oliver et al. |

FOREIGN PATENT DOCUMENTS

| EP | 0 872 255 A1 | 10/1998 |
| EP | 1 655 051 A1 | 5/2006 |
| JP | 2005034547 | 2/2005 |
| WO | WO 01/37914 A1 | 5/2001 |
| WO | WO 2006/050512 A2 | 5/2006 |
| WO | WO 2006/054210 A1 | 5/2006 |
| WO | WO 2006/090371 A2 | 8/2006 |
| WO | WO 2006/105085 A2 | 10/2006 |

OTHER PUBLICATIONS

Partial International Search issued in corresponding PCT application No. PCT/EP2007/063146, 3 pages, Aug. 4, 2008.
International Search Report and Written Opinion mailed Aug. 4, 2008 issued in corresponding international application No. PCT/EP2007/063146, 22 pages.

*Primary Examiner*—John P Lacyk
(74) *Attorney, Agent, or Firm*—Harrity & Harrity, LLP

(57) ABSTRACT

A device for inducing a target physiological state in a user may include a portable device including at least one receiver for receiving measurement data indicative of a current physiological state of the user, a processing unit for processing the received measurement data, at least one audio output unit and a memory, the processing unit being arranged to detect the current physiological state of the user by comparing the processed received measurement data to predefined data in the memory indicative of physiological states, wherein the processing unit is arranged to output audio data through the audio output unit depending on the detected current physiological state and to adjust the output of the audio data according to the target physiological state to be induced in the user.

25 Claims, 2 Drawing Sheets

SLEEPING MODE ACCESSORY

FIELD OF THE INVENTION

Embodiments disclosed herein may relate to measurement accessories. In particular, embodiments may relate to measurement accessories in portable units. In particular, embodiments may relate to the interaction between a measurement accessory and a main unit.

BACKGROUND

Presently, several systems interacting with a user in order to aid the user in reaching a certain physiological state or aiding the user in order to achieve certain goals related to physical exercise are known. As an example, biofeedback devices are on the market, which monitor the physiological state of the user via sensors and use music or sounds as feedback to the user in order to facilitate the user falling into the sleep state. Such systems may be bulky and expensive and may not be portable. One other drawback may be they are basically constructed to perform only function, i.e. the biofeedback.

Apart from biofeedback and portable feedback systems, known portable measurement devices may monitor physiological parameters, such the already mentioned heart rate, muscle tension, pulse, temperature and other parameters.

SUMMARY

In one embodiment, a portable device may indicate a target physiological state in a user, where the device may comprise at least one receiver for receiving measurement data indicative of the current physiological state of the user, a processing unit for processing the received measurement data and at least one audio output unit and a memory, where the processing unit is arranged to detect the current physiological state of the user by comparing the processed received measurement data to predefined data in the memory indicative of well-defined physiological states, wherein the processing unit is arranged to output audio data through the audio output unit depending on the detected actual physiological state and to adjust the output of the audio data according to the target physiological state to be induced in the user.

In this fashion a desired physiological state, such as relaxation, sleep, heightened concentration or other states can easily be induced in the user by a lightweight portable device which the user can carry everywhere. At the same time the actual physiological state of the user may also affect the state of the portable device.

According to another aspect of one embodiment, a system for inducing a target physiological state in a user may comprise a portable main unit and an accessory unit, where the main unit may comprise at least a receiver for receiving measurement data from the accessory unit, wherein the measurement data is indicative of the current physiological state of the user, a processing unit for processing the received measurement data, at least one audio output unit and a memory, where the processing unit is arranged to determine the current physiological state of the user by comparing the received measurement data to known data in the memory and to output audio data from the audio output unit depending on the detected physiological state, where the accessory unit may comprise a sensing unit for measuring data indicative of the current physiological state of the user of the main unit and a transmitter for transmitting the measured data to the main unit.

According to yet another aspect of one embodiment, an accessory unit for inducing a target physiological state in a user may use the accessory unit, where the accessory unit may comprise a sensing unit for measuring data indicative of the current physiological state of the user, a transmitter for transmitting the measured data via a wireless link and wherein the accessory unit further may comprise a receiver for wirelessly receiving control signals controlling the time interval of the measurement.

The accessory unit may be used together with the portable device described earlier and in a system for inducing a target physiological state in a user described above.

According to yet another aspect of one embodiment, a method for inducing a target physiological state in a user may include using a portable main unit comprising: a) receiving measurement data indicative of the current physiological state of a user of the main unit; b) processing the received measurement data; c) detecting the current physiological state of the user by comparing the processed received measurement data to predefined data in the memory indicative of well-defined physiological states; d) outputting audio data through an audio output unit; e) adjusting the output of the audio data according to the target physiological state to be induced in the user.

It should be mentioned here, that the portable device described earlier may be suitable for implementing a method according to one embodiment described above.

According to another aspect of one embodiment, a computer program for inducing a target physiological state in a user may use a portable unit comprising instructions sets for: a) receiving measurement data indicative of the current physiological state of a user of the main unit; b) processing the received measurement data; c) detecting the current physiological state of the user by comparing the processed received measurement data to predefined data in the memory indicative of well-defined physiological states; d) outputting audio data through an audio output unit and, e) adjusting the output of the audio data according to the target physiological state to be induced in the user.

The computer program may be suited to execute a method stated above and to be executed in a portable device according to one embodiment the described earlier.

DETAILED DESCRIPTION OF PREFERRED EMBODIMENTS

Figure 1:
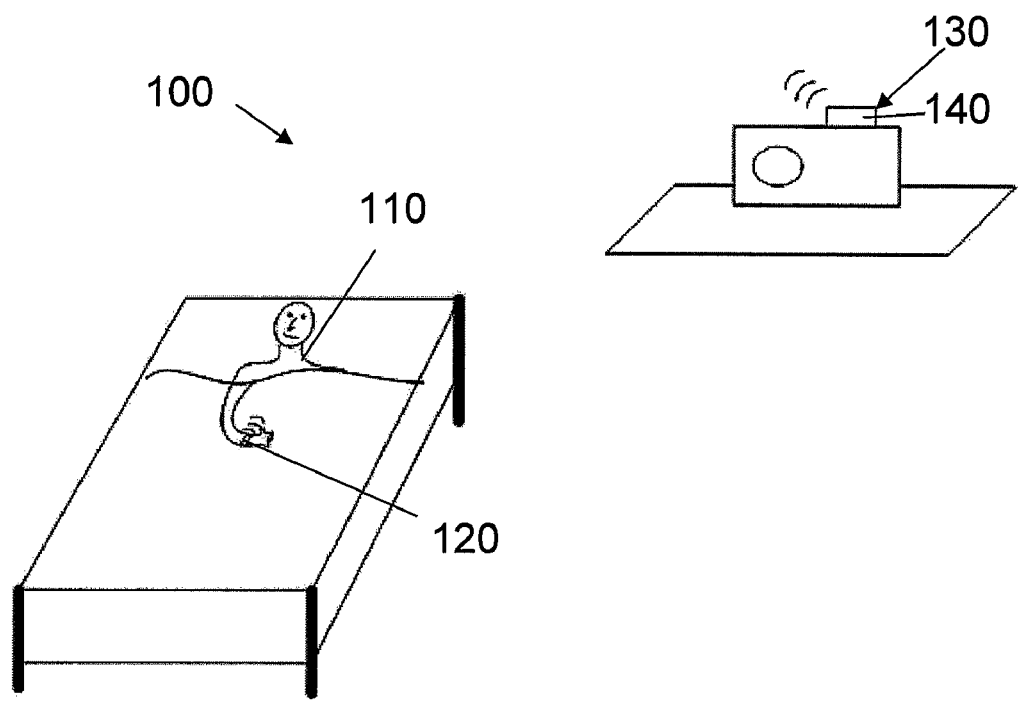
FIG. 1 illustrates an exemplary system according to one embodiment.

FIG. 1 illustrates an exemplary system 100 for relaxation and for inducing a sleep mode in a user 110 by means of a main unit 130 and an accessory unit 120 connected to the apparatus 130.

The user 110 in this example wears the accessory unit 120 in the form of a wristband on his or her wrist, where the sensor accessory registers the pulse rate of the user and sends the measurement data to the main unit 130. The accessory unit 120 may also be part of a wrist watch or may comprise a Velcro band. The accessory unit 120 may have a firm contact with the user's wrist in order to be able to accurately measure the user's pulse rate.

The accessory unit 120 in this example may be connected to the main unit 130 via a wireless link, such as for example a radio link, bluetooth, infrared, an IEEE 802series connection (0.11, 0.15, 0.16 with sub standards a, b, g or n, for example) or some other wireless connection standard as long as it is suitable for transferring digital or analog data. However, the link between the wristband 120 and the main unit 130 may also be a wired link via a copper or an optical fiber cable or some other suitable wired connection.

It should be mentioned that when using the infrared link, a reasonable line of sight angle and distance may be maintained between the accessory unit 120 and the main unit 130.

A main unit 130 located a distance away from the sensor accessory may receive the measurement signals or data from the accessory unit 120 via its receiver 140.

As a reaction to the received measurement signals or data which indicate the current physiological state of the user the main unit 130 either may remain in the present mode of operation or may change to a sleep mode. The sleep mode may be activated if the heart rate of the user 110 falls below a certain predefined value, where the main unit 130, for example, may switch to an analog or digital radio station with soothing or relaxing music. The main music may also play music or sound(s) stored in its memory (not shown) in case the main unit 130 is equipped with a memory.

Besides being a radio unit, the main unit 130, may also comprise any other device capable of radio or data communication and producing sounds or music. Also, the main unit 130 may, instead of being equipped solely with a receiver 140, also may include a transmitter (not shown) for controlling the accessory unit 120 in order to control the measurement interval or the measurement method. Also, a transmitter may be of use if the user desires to reach a certain target physiological state, such as relaxation, sleep but also other states, such as concentration or creativity so that the main unit 130 may signal to the accessory unit when to start the measurement.

Other means of measuring the physiological state of the user are possible, besides the measuring of the pulse rate. These measurements, such as measurements of the heart rate, breathing rate or other physiological parameters related to relaxation of the body may lead to a somewhat different construction of the accessory unit 120 and be provided as a torso band and/or be equipped with a microphone.

Apart from the variants above, the accessory unit 120 may be adapted to start measuring data indicative of the current physiological state of the user as soon as the user starts wearing it.

Figure 2:
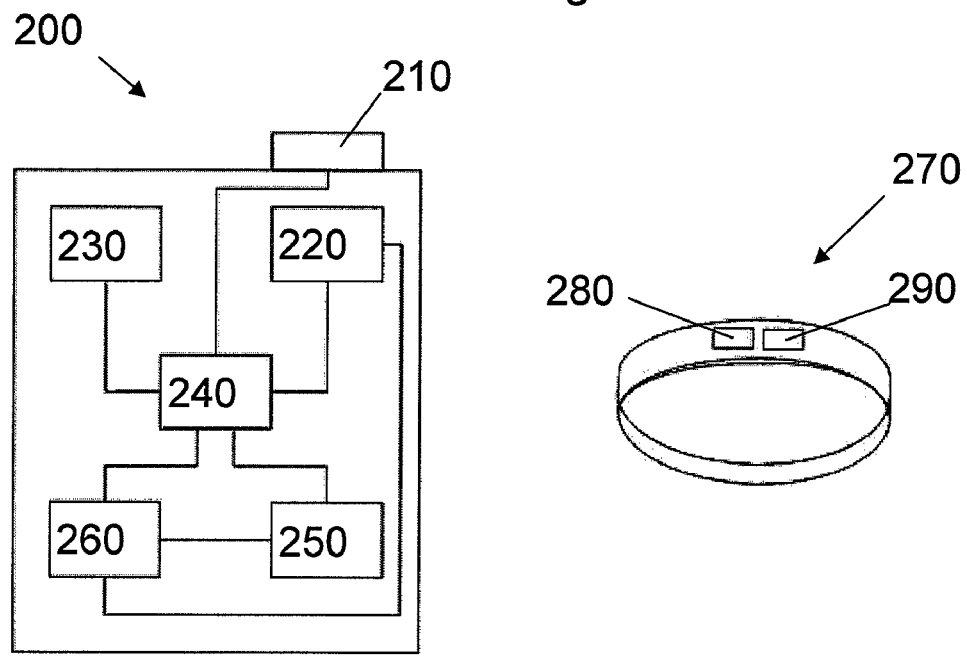
FIG. 2 illustrates an embodiment of the system.

Turning now to FIG. 2, a portable main unit 200 and an associated accessory unit 270 according to one embodiment are schematically illustrated in the figure. The main unit 200 may comprise a portable terminal 200 equipped with a transceiver 210, at least one audio output unit 220, at least one display 230, a processing unit 240, a memory 250 and a user interface 260. The term "portable" should be interpreted here as having such a weight and size that it can be carried by a human hand.

Accessory unit 270 may comprise at least one measurement sensor 270 and a transmitter 280. Apart from these two elements, the accessory unit 270 may also comprise a power source (not shown) in case it is operating on a wireless link with the portable terminal 200.

In the following, the function of the portable terminal 200 and its accessory 270 is explained in more detail. By means of the transceiver 210, the portable terminal 200 may receive measurement data which may indicate the current physiological state of the user, where the measurement data may be registered by the measurement sensors 280 of the accessory unit 270. This data may either be analog or digital signals. Measurement data, such as the pulse rate of the user 110 may be transferred by means of the transmitter 290 to the receiver 210 of the portable terminal 200. However, the portable terminal 270 may also comprise a receiver, which may be integrated together with the transmitter 280 if, for example, changes of the sampling interval (if the registered pulse rate signals are to be digitized) are to be controlled by the terminal 200 or changed to some other parameters.

A receiver may also be used if the measurement is to be initiated by the main unit 200. The processing unit 240 in this example may perform a digital-to-analog conversion of the measurement signals received from the accessory unit 270 if they are received in analog form. The processing unit 240 may further perform processing on the received signals, such as amplification and filtering, in order to be able to obtain accurate processing results in later processing stages.

The processing unit 240 in FIG. 2 may also be connected to a memory 250, where data in the form of different music or sounds as well as certain graphical diagrams or threshold values related to known physiological states of a human being are stored. The memory 250 may be an internal ROM (Read-Only-Memory) such as a FLASH-ROM or non-flashable ROM or a type of RAM (Random Access Memory), such as a memory card, hard disk, SIM-card or some built-in RAM-memory known to the skilled person. As far as the data, music and sounds in the memory 250 are concerned, it may either be pre-stored in the memory or downloaded and defined by the user of the portable terminal 200. Comparison of the signals received at the receiver 210 and processed in the processing unit 240 with the threshold values in the memory may give clues about the actual physiological state of the user of the accessory unit. Thereafter, the processing unit 240 may take appropriate action, such as playing music from the memory 250 over the audio output unit 220 of the portable terminal 200 and/or visualizing the received measurement data registered by the accessory unit 270 on the display 230 of the portable terminal 200.

If the accessory unit 270 of the main unit 200 comprises head phones, the music or sounds may be played via the head phones.

Also, the state of the portable unit 200 may be altered if an altered state of the user is detected, such as decreasing pulse-, heart- or breathing rate. This altered state of the portable unit 200 may express itself through decreasing the volume of the music or the sounds and/or slowing down of the speed with which they are played. It may also result in decreasing the background lighting to the display 220 of the portable unit 200.

Apart from the elements mentioned above, the main unit 200 may also comprise a user interface 260 allowing the user to choose from different target physiological states he or she wishes to achieve, such as a station of relaxation, a sleeping state or states of concentration or heightened creativity to name a few examples. Using a display 230

Also, the user may, via the user interface 260, define the time interval for the measurements of data indicating his or her current physiological state. The accessory unit 270 additionally may comprise a receiver (not shown) that is able to receive control information from the main unit 200 about the length of the measurement interval. However, the user may also set the measurement method to intermittent instead of continuous, as desired.

In case the portable terminal 200 also performs the function of a mobile terminal, the portable terminal 200 may change into a sleep mode, where incoming calls or messages may be registered but no audio- or visual indication of their reception may be signalled to the user.

Additionally, the accessory unit 270 may, like the sensor unit 280 and the receiver 290, also comprise an audio output unit of its own (not shown) for outputting music or sound to the user. Such an accessory unit may, for example, comprise head phones in addition to a wristband described earlier. It also may comprise a headset, i.e. a headphone/microphone combination for measuring the breathing rate of the user. In this fashion, the accessory unit 270 may receive control signals from the main unit 200 for outputting music or sound files from the memory 250 of the main unit 200 depending on the measurement data sent to the main unit 200. The control signals from the main unit 200 may also comprise instructions to the accessory unit to adjust the music or sounds played to the user in order to reach a target physiological state described earlier.

Figure 3:
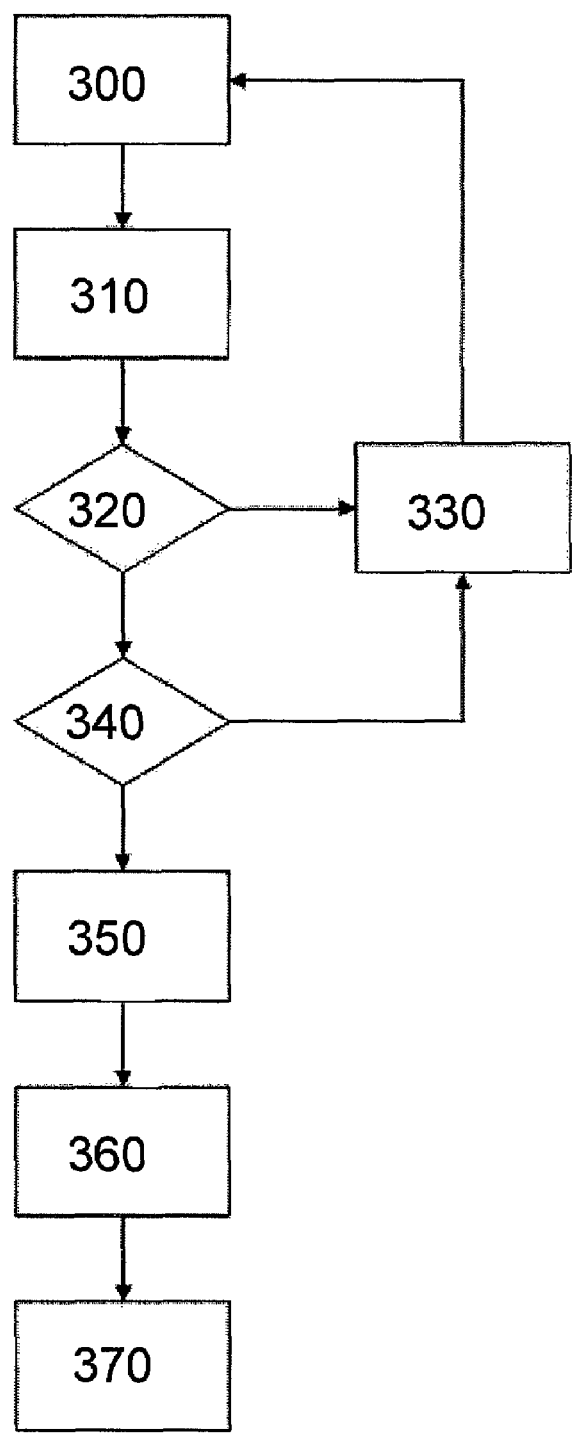
FIG. 3 illustrates an exemplary process of an embodiment.

Turning now to FIG. 3 an exemplary process according to one embodiment is illustrated. At block 300, an accessory unit, such as the accessory unit 260 in FIG. 2, may perform measurements of parameters which indicate the current physiological state of the user using the accessory unit. These parameters may range from pulse-, heart- or breathing rate to blood pressure and other parameters indicative of the physiological state of the user.

Thereafter, at block 310, the measured data may be transmitted to a portable unit, such as the portable unit 200 in FIG. 2 and received there. The communication between the accessory unit 260 and the portable unit 200 may take place either via a wireless link, such as via Bluetooth, IEEE 802.series (0.11, 0.15, 0.16, and sub standards a, b, g, n), Infrared or by wired communication, such as via cable or optical fibers.

At block 320, a processing unit in the portable unit, such as the processing unit 240, may analyze the received measurement data, and may convert the data to digital form by analog-to-digital conversion, may perform amplification and filtering of the signal and may compare the thus converted signal with a predefined first threshold value or a first graphical diagram. The predefined first threshold value or graphical diagram may be related to a certain known physiological state of a human being, such as for example when he or she is relaxed or close to the sleeping state. The threshold value or graphical diagram may be predefined by the manufacturer of the portable terminal 200, but also may be altered or downloaded by the user.

If the measurement signal received from the accessory unit 260 is above the predefined first threshold, the processing unit may retrieve music or sounds from a memory of the portable unit at block 330, such as the memory 250 in FIG. 2 and may instruct an audio output unit, such as the loudspeaker 230 in FIG. 2 to output the music or sound audibly to the user.

The music or sounds stored in the memory of the portable unit may be chosen so that they will have a relaxing and possibly sleep inducing effect on the user. However, in other embodiments of the method (not shown), the music may be chosen to induce a state of heightened concentration or creativity in the individual.

However, if the measurement signal received is determined to be below the predefined first threshold value, the processing unit may compare the measurement signal to a predefined second threshold value, where the predefined second threshold value may, for example, indicate whether the user is asleep or not. In the case that the received measurement value is above the predefined second threshold value, which may indicate that the user is relaxed but not sleeping, the processing unit 240, may at block 330 continue to play music or sounds from the memory 250 and may additionally reduce the volume and/or speed at which the music or sounds are played (not shown). In this fashion, a sleeping or an even more relaxed state in the user may be more easily induced.

If, however, the received measurement value through comparison with the predefined second threshold is determined to be below the predefined second threshold, the portable unit 350 may switch off the audio output unit 350 either by fading out the music or sounds or switching it off immediately. Hereby it may be possible to give the user of the portable unit the choice to define the fade-out period in advance or to set it to immediate turn-off.

At block 360 the portable unit 200 may change to sleep mode, which for example may comprise turning off its display, such as the display 220 in FIG. 2 and other audio-visual functions.

Finally, if the portable terminal comprises functionality for receiving telephone calls or electronic messages, the portable terminal may at block 370 switch to a state where calls or messages are received and registered, but where no audible or visual indications of the receipt are presented to the user.

While the embodiment of the method has been described for the case where the measurements are performed automatically on the user, the user may also define on the main unit that he wishes to reach a target state of relaxation or sleep or some other physiological state, such as heightened concentration or creativity. The main unit 200 may then signal to the accessory unit 260 to initiate measurement of the parameters indicated above and use music or sounds to facilitate for the user to reach the desired target state.

In the method described above, the measurements performed by the accessory unit may be continuous or intermittent. The measurement interval may also be defined by the user.

Also, the operations performed in the method of FIG. 3 may be suited to be executed by a computer program that is either stored in the memory of a portable terminal, such as the memory 250 of the portable terminal 200, or may be downloaded to the memory 250 from an external source, such as a communication network.

It is understood that various modifications of the present invention may be performed by the skilled person who has studied the description and the accompanying drawings within the scope defined by the claims.

The invention claimed is:

1. A portable device for inducing a target sleep state in a user, the device comprising:
   at least one receiver for receiving measurement data indicative of a current sleep state of the user,
   a processing unit for processing the received measurement data,
   at least one audio output unit and a memory,
   the processing unit to:
      detect the current sleep state of the user by comparing the processed received measurement data with predefined data in the memory indicative of sleep states,
      output audio data through the audio output unit depending on the detected current sleep state,
      adjust the output of the audio data according to a target sleep state to be induced in the user,
      detect that the user has fallen asleep, and
      switch off the output of the audio data in response to detecting that the user has fallen asleep.

2. The device according to claim 1, further comprising a user interface via which the user defines the predefined data in the memory indicative of sleep states and selects the target sleep state.

3. The device according to claims 2, further comprising a display unit for displaying visual data indicative of the current sleep state of the user.

4. The device according claims 1, further comprising a transmitter that connects the main unit to a wireless communication network.

5. The device according to claim 4, arranged to switch to a predefined state when the target sleep state has been induced.

6. The device according to claim 5, where the device is portable.

7. The device according to claim 1, where the received measurement data comprises analog data.

8. The device according to claim 7, where the processing unit is arranged to amplify and filter the analog sleep data before converting the analog sleep data into digital data.

9. The device according to claims 6 where the received measurement data comprises digital data.

10. The device according to claim 1, where the measurement data indicative of the current sleep state of the user comprises the pulse, heart rate, breathing rate, blood pressure or some other parameter suitable for indicating the sleep state of the user.

11. The device according to claim 10, where the predefined data in the memory indicative of sleep states comprises at least one threshold value or at least one graphical diagram indicative of a known sleep state in a human being.

12. The device according to claim 1, where the at least one audio output unit comprises a loudspeaker, headphones or some other unit suitable for audio output.

13. The device according to claim 12, where the audio data from the memory comprises musical or audio files.

14. The device according to claim 1, where the measurement data indicative of the sleep state of the user is received continuously.

15. The device according to claim 1, where the measurement data indicative of the sleep state of the user is received intermittently.

16. A system for inducing a target sleep state in a user comprising
a portable device according to claim 1, and
an accessory unit,
the accessory unit comprising
a sensing unit for measuring data indicative of the current sleep state of the user of the portable device, and
a transmitter for transmitting the measured data to the portable device.

17. The system according to claim 16, where the accessory unit is adapted to be worn by the user of the portable device.

18. The system according to claim 17, where the accessory unit is to obtain measurements of data indicative of the current sleep state of the user as soon as the accessory unit is worn by the user.

19. The system according to claim 17, where the accessory unit further comprises a receiver for receiving control information from the portable device.

20. The system according to claim 19, where the control information comprises information on parameters to be measured by the accessory unit or information on a measurement interval.

21. The system according to claim 16, where the accessory unit further comprises
a receiver for wirelessly receiving control signals controlling a time interval of the measurement.

22. The system according to claim 21, where the accessory unit further comprises an audio output unit for outputting wirelessly received music or sound to the user.

23. The system according to claim 22, where the receiver is further to wirelessly receive control signals controlling the output of the music or sound through the output unit depending on the measured current sleep state of the user and to adjust the output of the audio data according to the target sleep state to be induced in the user.

24. A method for inducing a target sleep state in a user using a portable main unit comprising:
receiving, by a sensor associated with the portable main unit, measurement data indicative of a current sleep state of a user of the portable main unit;
processing, by a processor of the portable main unit, the received measurement data;
detecting, by the processor, the current sleep state of the user by comparing the processed received measurement data to predefined data, in a memory, indicative of sleep states;
outputting audio data through an audio output unit based on the current sleep state;
adjusting, by the processor, the output of the audio data according to the target sleep state to be induced in the user;
detecting, by the processor, that the user has fallen asleep, and switching off, by the processor, the output of the audio data in response to detecting that the user has fallen asleep.

25. A memory device storing instructions for execution by a processer, comprising instructions for:
receiving measurement data indicative of a current sleep state of a user of a main unit;
processing the received measurement data;
detecting the current sleep state of the user by comparing the processed received measurement data to predefined data, in a memory, indicative of sleep states;
outputting audio data through an audio output unit based on the current sleep state;
adjusting the output of the audio data according to a target sleep state to be induced in the user;
detecting that the user has fallen asleep, and
switching off the output of the audio data in response to detecting that the user has fallen asleep.

* * * * *

UNITED STATES PATENT AND TRADEMARK OFFICE
CERTIFICATE OF CORRECTION

| | | |
|---|---|---|
| PATENT NO. | : 7,637,859 B2 | Page 1 of 1 |
| APPLICATION NO. | : 11/760420 | |
| DATED | : December 29, 2009 | |
| INVENTOR(S) | : Maria Lindbäck et al. | |

It is certified that error appears in the above-identified patent and that said Letters Patent is hereby corrected as shown below:

Column 6, line 65, after "to", delete "claims" and insert --claim--;

Column 7, line 1, after "according", delete "claims" and insert --to claim--;

Column 7, line 13, after "to", delete "claims 6" and insert --claim 6,--;

Column 8, line 34, after "and" delete "," and insert --;--;

Column 8, line 35, after "and", delete "switching off, by the processor, the output of the"; and Column 8, line 36, before "audio", insert --switching off, by the processor, the output of the--.

Signed and Sealed this

Twenty-seventh Day of July, 2010

David J. Kappos
*Director of the United States Patent and Trademark Office*